US012201667B2

(12) United States Patent
Chang et al.

(10) Patent No.: US 12,201,667 B2
(45) Date of Patent: Jan. 21, 2025

(54) FORMULATIONS FOR TREATING CRAMPS AND SPASMS

(71) Applicant: LYTONE ENTERPRISE, INC., New Taipei (TW)

(72) Inventors: William Tienhung Chang, New Taipei (TW); Vivian Weiting Chang, New Taipei (TW); Yu Hu, New Taipei (TW)

(73) Assignee: LYTONE ENTERPRISE, INC., New Taipei (TW)

( * ) Notice: Subject to any disclaimer, the term of this patent is extended or adjusted under 35 U.S.C. 154(b) by 0 days.

(21) Appl. No.: 17/456,628

(22) Filed: Nov. 26, 2021

(65) Prior Publication Data

US 2022/0168380 A1 Jun. 2, 2022

Related U.S. Application Data

(60) Provisional application No. 63/118,775, filed on Nov. 27, 2020.

(51) Int. Cl.
*A61K 38/05* (2006.01)
*A61K 36/9066* (2006.01)
*A61K 45/06* (2006.01)

(52) U.S. Cl.
CPC .......... *A61K 38/05* (2013.01); *A61K 36/9066* (2013.01); *A61K 45/06* (2013.01)

(58) Field of Classification Search
CPC .... A61K 38/05; A61K 36/9066; A61K 45/06; A61K 35/10; A61K 35/57; A61K 31/12; A61K 31/4172; A61P 21/00; A61P 21/02
See application file for complete search history.

(56) References Cited

U.S. PATENT DOCUMENTS

| | | | | |
|---|---|---|---|---|
| 9,327,005 | B1 * | 5/2016 | Pietrzkowski | A61K 33/06 |
| 2004/0242491 | A1 * | 12/2004 | Chang | A61P 19/02 |
| | | | | 514/400 |
| 2015/0283163 | A1 | 10/2015 | Rayburn et al. | |

FOREIGN PATENT DOCUMENTS

| | | | | |
|---|---|---|---|---|
| CN | 102048117 | A | | 5/2011 |
| CN | 104043058 | A | | 9/2014 |
| CN | 110201019 | A | * | 9/2019 |
| JP | 2004359663 | A | | 12/2004 |
| WO | WO-2016149277 | A1 | * | 9/2016 ........... A23L 33/105 |

OTHER PUBLICATIONS

Nippon Meat Information page, examiner generated in internet archive: https://web.archive.org/web/20130706111054/https://www.rdc.nipponham.co.jp/material_eng/ma_cbex.html (Year: 2013).*
Imaizumi, Highly bioavailable curcumin (Theracurmin): its development and clinical application, PharmaNutrition 3: 123-130. (Year : 2015).*
Katakura et al., Anserine/Carnosine Supplementation Suppresses the Expression of the Inflammatory Chemokine CCL24 in Peripheral Blood Mononuclear Cells from Elderly People; Nutrients; 9, 1199; doi:10.3390/nu9111199. (Year: 2017).*
Theracurmin Super corporate announcement 2017, Generated by examiner Dec. 22, 2022 (Year: 2017).*
Syeda T. Ahmed, Lyndsey Craven, Oliver M. Russell, Doug Turnbull, & Amy E. Vincent, Diagnosis and Treatment of Mitochondrial Myopathies, Neurotherapeutics 15:943-953 https://doi.org/10.1007/s13311-018-00674-4 (Year: 2018).*
Kiyani et al., Evaluation of Turmeric Nanoparticles as Anti-Gout Agent: Modernization of a Traditional Drug, Medicina;55(10); doi: 10.3390/medicina55010010. (Year: 2019).*
Diener HC, Dethlefsen U, Dethlefsen-Gruber S, Verbeek P. Effectiveness of quinine in treating muscle cramps: a double-blind, placebo-controlled, parallel-group, multicentre trial. Int J Clin Pract. May 2002;56(4):243-6. PMID: 12074203. (Year: 2002).*
Bhimani R, Anderson L. Clinical understanding of spasticity: implications for practice. Rehabil Res Pract. 2014;2014:279175. doi: 10.1155/2014/279175. Epub Sep. 4, 2014. PMID: 25276432; PMCID: PMC4168242. (Year: 2014).*
Chan, K. M. et al., "Extraction and activity of carnosine, a naturally occurring antioxidant in beef muscle," Journal of Food Science, vol. 58, No. 1, 1993, pp. 1-4.
Maikhunthod, B. and Intarapichet, K.-O., "Heat and ultrafiltration extraction of broiler meat carnosine and its antioxidant activity," Meat Science, 2005, 71, pp. 364-374.
Sato, M. et al., "Safety evaluation of chicken breast extract containing carnosine and anserine," Food and Chemical Toxicology, 46, 2008, pp. 480-489.
Zielinska, Aleksandra et al. "Properties, Extraction Methods, and Delivery Systems for Curcumin as a Natural Source of Beneficial Health Effects," Medicina, 2020, 56, 336.
Extended European Search Report dated May 10, 2022, issued in EP Patent Application No. 21210801.3.
J P H Fisher et al.: "Effective combination treatment of GD2-expressing neurobIsatoma and Ewing's sarcoma using anti-GD2 ch14.18/CHO antibody with Vy9Võ2+ yõT cells", ONCOIMMUNOLOGY, vol. 5, No. 1, Jan. 2, 2016 (Jan. 2, 2016).
Jordan M. Joy et al., "Supplementation with a proprietary blend of ancient peat and apple extract may improve body composition without affecting hematology in resistance-trained men", Appl. Physiol. Nutr. Metab., 40, 2015, 1171-1177.
Nelson Nicole L. et al., "A narrative review of exercise-associated muscle cramps: Factors that contribute to neuromuscular fatigue and management implications: Exercise-Associated Muscle Cramps", Muscle and Nerve, vol. 54, pp. 177-185 Aug. 2016.

(Continued)

*Primary Examiner* — Melissa L Fisher
*Assistant Examiner* — John Cronin
(74) *Attorney, Agent, or Firm* — Prosyla Group PC

(57) ABSTRACT

The present invention provides a formulation capable of treating cramp and/or spasm in a subject, or reducing frequency of cramp and/or spasm in a subject, wherein the formulation comprises a dipeptide composition containing one or more imidazole-containing dipeptides, a turmeric product containing curcumin, and ancient peat minerals.

16 Claims, 4 Drawing Sheets

(56) References Cited

OTHER PUBLICATIONS

Office Action dated Sep. 8, 2022, issued in Taiwan Patent Application No. 110144364. English Translation of Search Report included.
Wen-Ching Huang et al., "Chicken Essence Improves Exercise Performance and Ameliorates Physical Fatigue", Nutrients, 2014, 6, 2681-2696.
Wen-Ching Huang et al., "Effect of Curcumin Supplementation on Physiological Fatigue and Physical Performance in Mice", Nutrients, 2015, 7, 905-921.
Office Action issued in Japan Patent Application No. 2021-193063 on Feb. 8, 2023.
Sato, Kenichiro et al., "Production of Highly Purified Imidazole Dipeptides from Animal Extracts and Development of Foods to Prevent Lifestyle-Related Diseases," Japan Journal of Food Engineering, vol. 21, No. 3, p. 89-94.
Sato, Makoto et al., "Quality Valuation of Turmeric Powders on Market," Annual Report of the Mie Prefectural Institute of Public Health and Environment No. 6 (vol. 49) p. 52-54.
Sato, Mikako et al., "Effect of Long term Ingestion of Chicken Extract on Muscular Power for Middle and Advanced Age Groups," The Japanese Society for Food Science and Technology vol. 59, fourth p. 182-185.
Bagdara Farms Website: "Sportyheal-5x Relieving Muscle Spasms," website: https://bagdarafarms.com/spasms-treatment-with-turmeric/, pp. 1-2.
Gong111, Personal Library, "Market of more natural energy product (2)," website: http://www.360doc.com/content/17/0310/16/167211_635587201.shtml, pp. 1-2.
Itani, Rania et al., "Primary Dysmenorrhea: Pathophysiology, Diagnosis, and Treatment Updates," Korean J Fam Med, 2022, vol. 43, pp. 101-108.
Katzberg, Hans D., MD, MSc, FRCPC and Sadeghian, Hamid, MD FRCPC, "Muscle Cramps: Reliable and validated outcome measures and new treatments are needed," Neuromuscular Disorders, Practical Neurology, Jul./Aug. 2019, pp. e1-e6.
Office Action dated Mar. 29, 2024 issued in corresponding Chinese patent application No. 202111448008.0. English translation of Search Report included.

* cited by examiner

FORMULATIONS FOR TREATING CRAMPS AND SPASMS

CROSS REFERENCE TO RELATED APPLICATION

This application claims priority to and benefit of U.S. Provisional Application No. 63/118,775, filed Nov. 27, 2020, the disclosure of which is incorporated herein by reference in its entirety.

FIELD OF THE INVENTION

The present invention relates to a formulation for treating cramps and spasms, which comprises a dipeptide composition containing one or more imidazole-containing dipeptides, a turmeric product containing curcumin, and ancient peat minerals.

BACKGROUND OF THE INVENTION

Spasms and cramps are commonly thought to be due to muscle overuse, dehydration, or an electrolyte imbalance. A muscle cramp is similar to a spasm, but a cramp lasts longer than a spasm and is often a very forcible contraction. Cramps and spasms are often associated with pregnancy, physical exercise or overexertion, age (common in older adults), medical conditions (e.g., dystonia), or may be a sign of a motor neuron disorder. Cramps and spasms may occur in a skeletal muscle or smooth muscle. Skeletal muscle cramps/spasms may be caused by muscle fatigue or a lack of electrolytes such as sodium (a condition called hyponatremia), potassium (called hypokalemia), or magnesium (called hypomagnesemia). Cramps/spasms of smooth muscle may be due to menstruation or gastroenteritis. Motor neuron disorders (e.g., amyotrophic lateral sclerosis), metabolic disorders (e.g., liver failure), some medications (e.g., diuretics and inhaled β-agonists), and haemodialysis may also cause muscle cramps/spasms. Most commonly, a muscle cramp/spasm is accompanied by a sudden burst of pain.

Quinine is modestly effective in treating cramps and spasms. However, it was found that quinine reduces cramp frequency by only about a quarter. Furthermore, the usual therapeutic dose of quinine may cause a variety of adverse effects, including cinchonism, hypoglycemia, hypotension, hearing and visual disturbances, and hemolysis. In 2010, practice guidelines for American neurologists on the symptomatic management of muscle cramps concluded that, although likely effective, quinine should be avoided for routine use because of the potential for toxic effects. Botulinum toxin is known to be able to locally treat cramps. However, injection of botulinum toxin is an invasive treatment, and thus may reduce patient compliance; and botulinum toxin may cause adverse effects, such as redness and swelling, pain, and local muscle weakness. Therefore, there remains a need in the art for improving the conditions of cramps and spasms, or reducing frequency of occurrence.

SUMMARY OF INVENTION

Accordingly, the present invention provides a formulation to treat cramp and/or spasm in a subject, and/or to reduce frequency of cramp and/or spasm in a subject.

One aspect of the invention relates to a formulation comprising a dipeptide composition containing >10% w/w of one or more imidazole-containing dipeptides based on the total weight of the composition, a turmeric product containing >15% w/w of curcumin based on the total weight of the extract, and ancient peat minerals; and optionally one or more carriers or excipients.

One aspect of the invention relates to the use of the formulation of the present invention in a method for treating cramp in a subject in need, wherein the method comprises administering a therapeutically effective amount of the formulation of the present invention to the subject.

One aspect of the invention relates to use of the formulation of the present invention in a method for treating spasm in a subject in need, wherein the method comprises administering a therapeutically effective amount of the formulation of the present invention to the subject.

One aspect of the invention relates to use of the formulation of the present invention in a method for reducing frequency of cramp in a subject in need, wherein the method comprises administering a therapeutically effective amount of the formulation of the present invention to the subject.

One aspect of the invention relates to use of the formulation of the present invention in a method for reducing frequency of spasm in a subject in need, wherein the method comprises administering a therapeutically effective amount of the formulation of the present invention to the subject.

Other aspects of the invention will become apparent from the following description.

DETAILED DESCRIPTION

Figure 1:
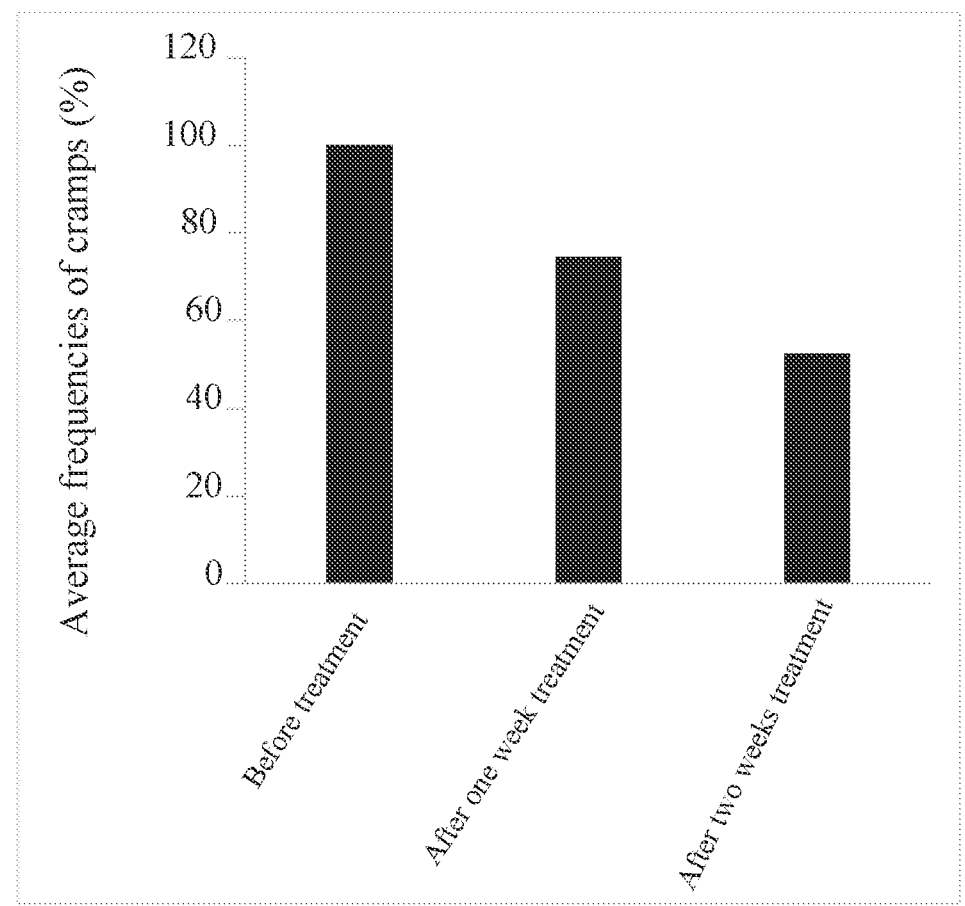
FIG. 1 shows the average frequencies of cramps in patients before and after treatment.

It must be noted that, as used in the specification and the appended claims, the singular forms "a," "an" and "the" include plural referents unless the context clearly dictates otherwise. Thus, unless otherwise required by context, singular terms shall include the plural and plural terms shall include the singular.

Often, ranges are expressed herein as from "about" one particular value and/or to "about" another particular value. When such a range is expressed, an embodiment includes the range from the one particular value and/or to the other particular value. Similarly, when values are expressed as approximations, by use of the word "about," it will be understood that the particular value forms another embodiment. It will be further understood that the endpoints of each of the ranges are significant both in relation to and independently of the other endpoint. As used herein the term "about" refers to ±20%, ±15%, ±10%, ±9%, ±8%, ±7%, ±6%, ±5%, ±4%, ±3%, ±2%, ±1%, ±0.5%, or ±0.25%.

"Optional" or "optionally" means that the subsequently described event or circumstance may or may not occur, and that the description includes instances where said event or circumstance occurs and instances where it does not. For example, the phrase "optionally comprising an agent" means that the agent may or may not exist.

The term "carrier" or "excipient" as used herein refers to any substance, not itself a therapeutic agent, used as a carrier and/or diluent and/or adjuvant, or vehicle for delivery of a therapeutic agent to a subject or added to a formulation to improve its handling or storage properties or to permit or facilitate formation of a dose unit of the composition into a discrete article such as a capsule or tablet suitable for oral administration. Suitable carriers or excipients are well known to persons of ordinary skill in the art of manufacturing pharmaceutical formulations or food products. Carriers or excipients can include, by way of illustration and not limitation, buffers, diluents, disintegrants, binding agents, adhesives, wetting agents, polymers, lubricants, glidants, substances added to mask or counteract a disagreeable taste or odor, flavors, dyes, fragrances, and substances added to improve the appearance of the composition. Acceptable carriers or excipients include citrate buffer, phosphate buffer, acetate buffer, bicarbonate buffer, stearic acid, magnesium stearate, magnesium oxide, sodium and calcium salts of phosphoric and sulfuric acids, magnesium carbonate, talc, gelatin, acacia gum, sodium alginate, pectin, dextrin, mannitol, sorbitol, lactose, sucrose, starches, gelatin, cellulosic materials (such as cellulose esters of alkanoic acids and cellulose alkyl esters), low melting wax, cocoa butter, amino acids, urea, alcohols, ascorbic acid, phospholipids, proteins (for example, serum albumin), ethylenediamine tetraacetic acid (EDTA), dimethyl sulfoxide (DMSO), sodium chloride or other salts, liposomes, mannitol, sorbitol, glycerol or powder, polymers (such as polyvinyl-pyrrolidone, polyvinyl alcohol, and polyethylene glycols), and other pharmaceutically acceptable materials. The carrier or excipient should not destroy the pharmacological activity of the therapeutic agent and should be non-toxic when administered in doses sufficient to deliver a therapeutic amount of the agent. In a preferred embodiment, the carriers or excipient may provide an effervescent effect. In such case, the carriers or excipient comprises alkali metal carbonates (including carbonate and bicarbonate) and organic acids, which is in solid form at normal temperature. In the presences of a solvent, e.g., water, the alkaline carbonate together with the organic acid would generate carbon dioxide gas. Examples of the alkali metal carbonates compound include, but are not limited to $NaHCO_3$, $KHCO_3$, $CaCO_3$, $Na_2CO_3$, $K_2CO_3$, $MgCO_3$, $Ca(HCO_3)_2$, $CKNaO_3$, $C_2Na_3O_6$ (sodium sesquicarbonate) and $C_3H_4NNa_3O_5$ (sodium glycine carbonate). Examples of the organic acids include, but are not limited to tartaric acid, citric acid, fumaric acid, salicylic acid, oxalic acid, succinic acid, maleic acid, malic acid, glycolic acid, adipic acid, and any other suitable acid or acid anhydride.

The term "amino acid" refers to natural amino acids, unnatural amino acids, and amino acid analogs. Unless otherwise indicated, the term "amino acid" includes both D and L stereoisomers if the respective structure allows such stereoisomeric forms.

Natural amino acids include alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), Lysine (Lys or K), methionine (Met or M), phenylalanine (Phe or F), proline (Pro or P), serine (Ser or S), threonine (Thr or T), tryptophan (Trp or W), tyrosine (Tyr or Y) and valine (Val or V).

Unnatural amino acids, or non-natural amino acids include, but are not limited to, azetidinecarboxylic acid, 2-aminoadipic acid, 3-aminoadipic acid, beta-alanine, naphthylalanine ("naph"), aminopropionic acid, 2-aminobutyric acid, 4-aminobutyric acid, 6-aminocaproic acid, 2-aminoheptanoic acid, 2-aminoisobutyric acid, 3-aminoisbutyric acid, 2-aminopimelic acid, tertiary-butylglycine ("tBuG"), 2,4-diaminoisobutyric acid, desmosine, 2,2'-diaminopimelic acid, 2,3-diaminopropionic acid, N-ethylglycine, N-ethylasparagine, homoproline ("hPro" or "homoP"), hydroxylysine, allo-hydroxylysine, 3-hydroxyproline ("3Hyp"), 4-hydroxyproline ("4Hyp"), isodesmosine, allo-isoleucine, N-methylalanine ("MeAla" or "Nime"), Nalkylglycine ("NAG") including N-methylglycine, N-methylisoleucine, N-alkylpentylglycine ("NAPG") including N-methylpentylglycine. N-methylvaline, naphthylalanine, norvaline ("Norval"), norleucine ("Norleu"), octylglycine ("OctG"), ornithine ("Orn"), pentylglycine ("pG" or "PGly"), pipecolic acid, thioproline ("ThioP" or "tPro"), homoLysine ("hLys"), and homoArginine ("hArg").

In one aspect, the invention provides a formulation comprising a dipeptide composition containing >10% w/w of one or more imidazole-containing dipeptides based on the total weight of the composition, a turmeric product containing >15% w/w of curcumin based on the total weight of the product, and ancient peat minerals; and optionally one or more carriers or excipients.

In a preferred embodiment of the invention, the dipeptide composition contains, based on the total weight of the composition, about 10 to 40% w/w of one or more imidazole-containing dipeptides, and more preferably about 15 to 30% w/w of one or more imidazole-containing dipeptides.

As used herein, the term "dipeptide" refers to a peptide formed by two amino acids linked via an amide bond, also known as a peptide bond. The term "imidazole-containing dipeptide" refers to a dipeptide in which at least one amino acid contains an imidazole moiety; and the imidazole-containing amino acid may be presented at either the N-terminus or C-terminus of the dipeptide, or both terminuses of the dipeptide. In a preferred embodiment, the imidazole-containing amino acid is histidine. Examples of the imidazole-containing dipeptide include but are not limited to carnosine (β-alanyl-L-histidine) and anserine (β-alanyl-1-methyl-L-histidine).

According to the invention, the dipeptide composition may be a hydrolysate or extract of a natural substance, such as an animal, e.g., fish, chicken, or beef, or a plant, e.g., soy bean (K. M. Chan et al., "Extraction and activity of carnosine, a naturally occurring antioxidant in beef muscle," Journal of Food Science, Vol. 58, No. 1, 1993, pp. 1-4; B. Maikhunthod and K.-O. Intarapichet, "Heat and ultrafiltration extraction of broiler meat carnosine and its antioxidant activity," Meat Science, 2005, 71, pp. 364-374; and M. Sato et al., "Safety evaluation of chicken breast extract containing carnosine and anserine," Food and Chemical Toxicology, 46, 2008, pp. 480-489), or commercially available from such as NH Foods Ltd. and Yaizu Suisankagaku Industry Co., Ltd.

Curcumin (diferuloylmethane) is a major component of *Curcumin longa*, generically known as turmeric, which belongs to the ginger family (Zingiberaceae) of perennial plants that grows naturally in India and other parts of Asia. Curcumin has been proven as the active ingredient of turmeric for treating a wide variety of diseases, e.g., cancers, cardiovascular disease, obesity, inflammatory disease, and aging.

In a preferred embodiment of the invention, the turmeric product contains, based on the total weight of the product, about 15 to 50% w/w of curcumin, and more preferably about 30 to 40% w/w of curcumin. According to the invention, the turmeric product may be a dried turmeric powder, a turmeric extract, a sub-micron turmeric having a particle size ranging from 100 to 1000 nm, or a nano turmeric having a particle size ranging from 1 to 100 nm.

According to the invention, the turmeric product may be obtained by any methods known in the art, such as Aleksandra Zielinska et al. "Properties, Extraction Methods, and Delivery Systems for Curcumin as a Natural Source of Beneficial Health Effects," Medicina, 2020, 56, 336; and Hiroki Sasaki et al. "Innovative Preparation of Curcumin for Improved Oral Bioavailability," Biol. Pharm. Bull., 2011, 34(5) 660-665, or commercially available, for example from Theravalues Corporation.

According to the invention, ancient peat minerals are mineral nutrients (chemical elements) extracted from the peat deposited in the deep ocean bed. The ancient peat minerals are also extracted form plant derived minerals that come from a group of age old plant minerals that have been preserved for thousands of years between sandstone layers. Ancient peat minerals contain over 70 mineral nutrients and trace elements including aluminum, antimony, arsenic, barium, beryllium, bismuth, boron, bromine, cadmium, calcium, carbon, cerium, cesium, chloride, chromium, cobalt, copper, dysprosium, erbium, europium, fluoride, gadolinium, gallium, germanium, gold, hafnium, holmium, indium, iodine, iridium, iron, lanthanum, lead, lithium, lutetium, magnesium, manganese, mercury, molybdenum, neodymium, nickel, niobium, nitrogen, osmium, oxygen, palladium, phosphorus, platinum, potassium, praseodymium, rhenium, rhodium, rubidium, ruthenium, samarium, scandium, selenium, silicon, silver, sodium, strontium, sulfur, tantalum, tellurium, terbium, thallium, thorium, thulium, tin, titanium, tungsten, vanadium, ytterbium, yttrium, zinc, and zirconium. Ancient peat minerals are commercially available, for example from FutureCeuticals, Inc., and AZOMITE® Mineral Products, Inc.

According to the invention, the dipeptide composition is in an amount of about 0.5 to 10% w/w, preferably about 1 to 5% w/w, and more preferably about 2 to 3% w/w based on the total weight of the formulation; the turmeric product is in an amount of about 0.05 to 1.5% w/w, preferably about 0.1 to 0.4% w/w, and more preferably about 0.1 to 0.3% w/w based on the total weight of the formulation; and the ancient peat minerals are in an amount of about 0.05 to 5% w/w, preferably about 0.1 to 0.8% w/w, and more preferably about 0.1 to 0.5% w/w based on the total weight of the formulation.

Another embodiment of the invention relates to use of the formulation of the present invention in a method for treating cramp in a subject in need, wherein the method comprises administering a therapeutically effective amount of the formulation of the present invention to the subject.

Another embodiment of the invention relates to use of the formulation of the present invention in a method for treating spasm in a subject in need, wherein the method comprises administering a therapeutically effective amount of the formulation of the present invention to the subject.

Another embodiment of the invention relates to use of the formulation of the present invention in a method for reducing frequency of cramp in a subject in need, wherein the method comprises administering a therapeutically effective amount of the formulation of the present invention to the subject.

Another embodiment of the invention relates to use of the formulation of the present invention in a method for reducing frequency of spasm in a subject in need, wherein the method comprises administering a therapeutically effective amount of the formulation of the present invention to the subject.

The term "subject" as used herein denotes any animal, preferably a mammal, and more preferably a human. Examples of subjects include humans, non-human primates, rodents, guinea pigs, rabbits, sheep, pigs, goats, cows, horses, dogs and cats.

The term "effective amount" of an active ingredient as provided herein means a sufficient amount of the ingredient to provide the desired regulation of a desired function. As will be pointed out below, the exact amount required will vary from subject to subject, depending on the disease state, physical conditions, age, sex, species and weight of the subject, the specific identity and formulation of the composition, etc. Dosage regimens may be adjusted to induce the optimum therapeutic response. For example, several divided doses may be administered daily or the dose may be proportionally reduced as indicated by the exigencies of the therapeutic situation. Thus, it is not possible to specify an exact "effective amount." However, an appropriate effective amount can be determined by one of ordinary skill in the art using only routine experimentation. For example, in accordance with embodiments of the invention, an effective amount may range from 15 mg/Kg to 400 mg/Kg, preferably from 20 mg/Kg to 300 mg/Kg, more preferably from 30 mg/Kg to 200 mg/Kg, based on the weight of the subject.

The term "treating" or "treatment" as used herein denotes reversing, alleviating, inhibiting the progress of, or improving the disorder, disease or condition to which such term applies, or one or more symptoms of such disorder, disease or condition.

The term "frequency of cramp/spasm" as used herein denotes the relapse times at which cramp/spasm occurs in a subject during a period of time, e.g., in 6 hours, in 12 hours, in 18 hours, in 24 hours, during day time, at night, or in a day.

The term "reducing frequency of cramp/spasm" as used herein denotes reduction in the relapse times of cramp/spasm occurring in a subject after treatment during a period of time is, e.g., about a half, about one-third, about a quarter, or about one-fifth, of that of the subject before treatment; or cramp/spasm of a subject does not occur after treatment during a period of time.

The formulation can be administered in a variety of dosage forms including but not limited to a solid dosage form or a liquid dosage form, an oral dosage form, an intranasal dosage form, a lozenge, a troche, a controlled release dosage form, a pulsed release dosage form, an immediate release dosage form, a suspension, or combinations thereof. In one embodiment of the invention, the formulation is administered orally. For oral administration, the formulation will generally be provided in unit dosage form of a tablet, an effervescent tablet, pill, dragee, lozenge or capsule; as a powder, an effervescent powder or granules; or as an aqueous solution, suspension, liquid, gel, syrup, slurry, etc. suitable for ingestion by the subject.

Embodiments of the invention will be illustrated with the following specific examples. One skilled in the art would appreciate that these examples are for illustration only and that other modifications and variations are possible without departing from the scope of the invention.

EXAMPLES

The experiments were performed in an orthopedic clinic. In the experiments, the conditions of the subjects independently having night cramps, spasms caused by nerve damage, muscle fatigue, and neuromuscular disorders were determined by a doctor through inquiries. The data, including basic personal information, frequencies of cramp/spasm, levels of pain, durations of cramp/spasm, sleeping quality, and levels of sarcopenia, obtained from the inquiries performed for one to two weeks were evaluated by a method modified from Kuo-hsin Chan, Prevalence and Factors Associated with Nocturnal Leg Cramps among Adolescents, 2009, Department of Natural Biotechnology, Nanhua University, Chiayi, Taiwan.

Example 1. Preparation of Formulation A

Formulation A was prepared by mixing the components shown in Table 1.

TABLE 1

Components of Formulation A

| Components | % (w/w) |
| --- | --- |
| Chicken meat extract (containing >15% imidazole-containing dipeptides) (NH Foods Ltd.) | 2.44% |
| Turmeric extract (containing >30% curcumin) (Theravalues Corporation) | 0.24% |
| Ancient peat minerals (containing >70 kinds of trace elements) (FutureCeuticals, Inc.) | 0.49% |
| Anhydrous citric acid | 48.78% |
| Sodium hydrogen carbonate | 21.95% |
| Sorbitol powder | 18.54% |
| Polyethylene glycol | 5.85% |
| Sugar | 1.71% |
| Total: | 100.00% |

Example 2. Effects of Formulation a in Treating Night Cramps and Muscle Spasms Caused by Nervous Disorder Eight patients from 28 to 75 years old who independently suffered from night cramps and muscle spasms caused by nervous disorder and suffered cramps in the muscles of the feet, legs or hips an average of 4 to 5 times per week were studied in this test.

Figure 2:
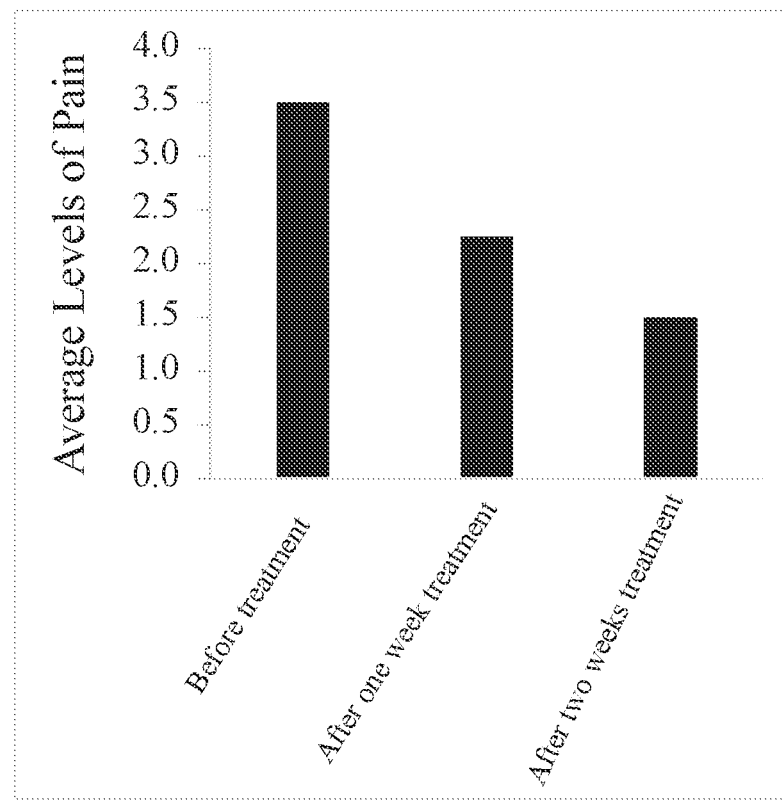
FIG. 2 shows the average levels of pain in the patients before and after treatment.
Figure 3:
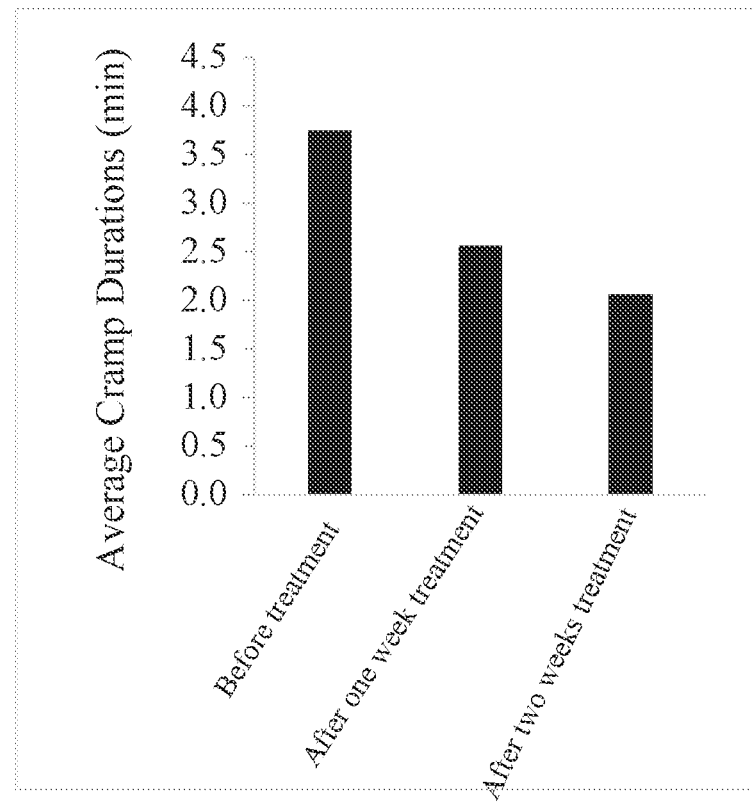
FIG. 3 shows the average cramp durations in the patients before and after treatment.

4.1 g of Formulation A was mixed with 150 ml water at room temperature to form Solution A; and Solution A was immediately taken by the patients before sleep. Such treatment was performed for two weeks. As can be seen from FIG. 1, after one week of treatment, the average frequency of cramps reduced 25.4%; and after two weeks of treatment, the average frequency of cramps reduced 47.6%. Degree of pain was measured by Face Rating Scale, and level 5 was used to represent the utmost degree. As can be seen from FIG. 2, before treatment, the average level of pain was 3.5; after one week of treatment, the average level dropped to 2.3 (a reduction of about 35.71%); and after two weeks of treatment, the average level dropped to 2.1 (reduction of about 57.14%). The duration of each cramp was also measured, and the results are shown in FIG. 3. As can be seen from FIG. 3, before treatment, the average cramp duration was 3.8 minutes; after one week of treatment, the average cramp duration lowered to 2.6 minutes; and after two weeks of treatment, the average cramp duration lowered to 2.1 minutes.

Figure 4:
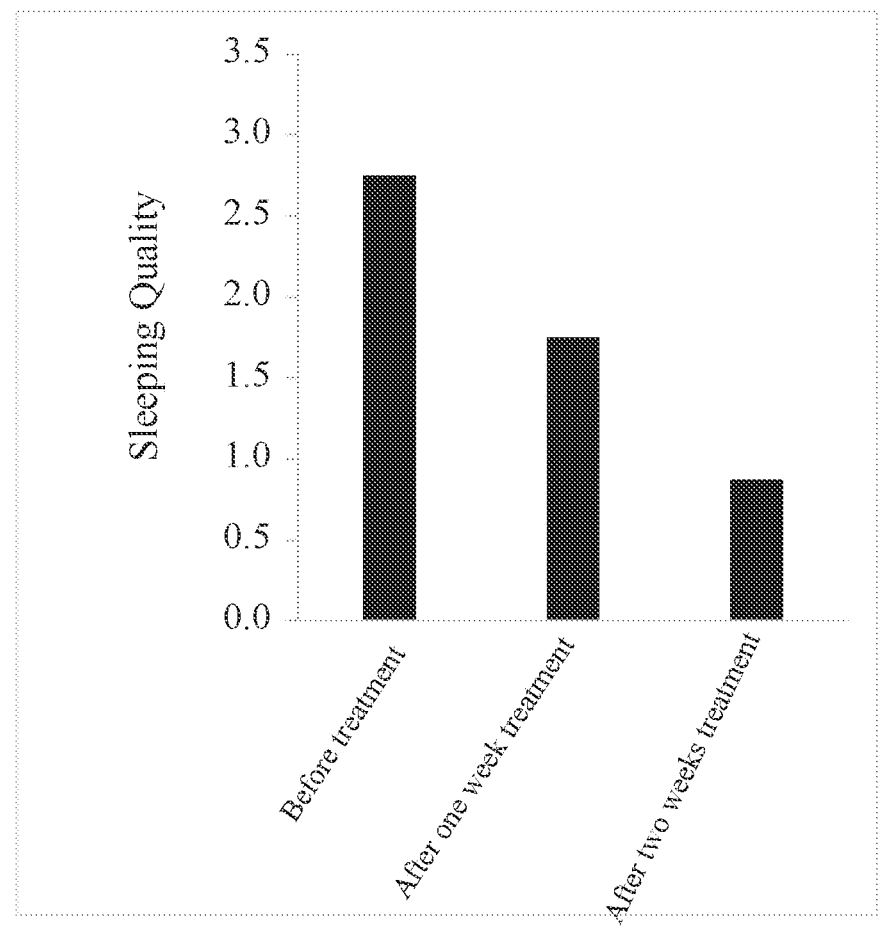
FIG. 4 shows the average levels of sleeping quality of the patients before and after treatment.

Example 3. Effect of Formulation a in Improving Sleep Quality 4.1 g of Formulation A was mixed with 150 ml water at room temperature to form Solution A; and Solution A was immediately taken by the patients suffering from night cramps before sleep. Such treatment was performed for two weeks. Level 5 was used to represent the worst sleep quality caused by night cramp interruptions. As can be seen from FIG. 4, before treatment, the average level of sleep quality was 2.8; after one week of treatment, the average level dropped to 1.8 (a reduction of about 36.4%); and after two weeks treatment, the average level dropped to 0.9 (a reduction of about 68.2%).

Example 4. Effect of Formulation a in Increasing Muscle Strength

Five patients independently suffering from night cramps and muscle spasms caused by nervous disorder were studied in this test. 4.1 g of Formulation A was mixed with 150 ml water at room temperature to form Solution A; and Solution A was taken by the patients when cramps occurred during the day time, and before sleep. Such treatments were performed for two weeks. The degree of sarcopenia was evaluated basically based on strength, assistance with walking, rising from a chair, climbing stairs, and falls (SARC-F), and level 6 was used to represent the utmost degree. As shown in Table 2 below, before treatment, the levels of sarcopenia of five patients were 1 to 3; after one week of treatment, the levels of three patients dropped to 0; and after two weeks of treatment, the level of another patient also dropped to 0.

TABLE 2

| | Levels of Sarcopenia | | |
| --- | --- | --- | --- |
| Subjects | Before Treatment | One Week Treatment | Two Weeks Treatment |
| 1 | 2 | 2 | 0 |
| 2 | 2 | 0 | 0 |
| 3 | 2 | 2 | 2 |
| 4 | 3 | 0 | 0 |
| 5 | 1 | 0 | 0 |

Example 5. Preparation of Formulation B

Formulation B was prepared by mixing the components shown in Table 3.

TABLE 3

Components of Formulation B

| Components | % (w/w) |
| --- | --- |
| Chicken meat extract (containing >15% imidazole-containing dipeptides) (NH Foods Ltd.) | 2.44% |
| Turmeric extract (containing >30% curcumin) (Theravalues Corporation) | 0.12% |
| Ancient peat minerals (containing >70 kinds of trace elements) (FutureCeuticals, Inc.) | 0.12% |
| Anhydrous citric acid | 46.34% |
| Sodium hydrogen carbonate | 19.51% |
| Sorbitol powder | 18.54% |
| Polyethylene glycol | 5.85% |
| Sugar | 1.46% |
| Sucralose | 0.24% |
| Acesulfame potassium | 0.49% |
| Orange spice | 3.66% |
| Ice cream soda spice | 1.22% |
| Total: | 100.00% |

Example 6. Effects of Formulation B in Quickly Relieving Cramp, Muscle Spasm, and Pain When a cramp occurred, 4.1 g Formulation B was dissolved in 150 ml water at room temperature to form Solution B; and Solution B was taken by the patients within 2 minutes of cramping. As shown in Table 4, cramps and pain in the patients disappeared within 0.5 to 2 minutes. Cramps and pain relapsed in some patients after 10 minutes of treatment. However, after retreated by a same treatment, cramps and pain did not recur. This suggests that the formulations of the invention can quickly relieve the syndromes caused by cramps, and reduce the chance of relapse.

TABLE 4

| Subjects | Gender | Ages | Time When Cramps or Spasms Occur | Locations of Cramps or Spasms | Duration of Cramps or Spasms before Treatment | Time Taken to Relieve Cramps or Spasms after Treatment | Duration of Cramps or Spasms after Treatment | Relapse Times of Cramps before Treatment | Relapse Times of Cramps after Treatment |
|---|---|---|---|---|---|---|---|---|---|
| 9 | Male | 75 | night and after exercising | thigh | 8-10 min | 0.5 min | 1 min | 4-5 | <1 |
| 10 | Female | 71 | night | lower leg | 10-20 min | 1 min | 2 min | 3-4 | <1 |
| 11 | Male | 45 | night | lower leg | 10-20 min | 1 min | 2 min | 4-5 | <1 |
| 12 | Female | 40 | menstruation | uterus | 1 day | 2 min | 2 min | 3-4 | 0 |

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. A method for treating cramp caused by a neuron disorder or during menstruation in a subject in need thereof, wherein the method comprises administering a therapeutically effective amount of a formulation to the subject,
    wherein the formulation comprises a dipeptide composition comprising >10%, w/w of one or more imidazole-containing dipeptides based on the total weight of the dipeptide composition, a turmeric product comprising >15% w/w of curcumin based on the total weight of the turmeric product and ancient peat minerals, and optionally one or more carriers or excipients;
    wherein the dipeptide composition is in an amount of about 0.5 to 10% w/w based on the total weight of the formulation, wherein the turmeric product is in an amount of about 0.05 to 1.5% w/w based on the total weight of the formulation, wherein peat minerals are in an amount of about 0.05 to 5% w/w based on the total weight of the formulation, and
    wherein the treatment reduces the frequency or duration of cramp, or reduces the degree of pain.

2. A method for treating spasm caused by a neuron disorder or during menstruation in a subject in need thereof, wherein the method comprises administering a therapeutically effective amount of a formulation to the subject,
    wherein the formulation comprises a dipeptide composition comprising >10% w/w of one or more imidazole-containing dipeptides based on the total weight of the dipeptide composition, a turmeric product comprising >15% w/w of curcumin based on the total weight of the turmeric product, and ancient peat minerals, and optionally, one or more carriers or excipients;
    wherein the dipeptide composition is in an amount of about 0.5 to 10% why based on the total weight of the formulation, wherein the turmeric product is in an amount of about 0.05 to 1.5% w/w based on the total weight of the formulation, wherein the ancient peat minerals are in an amount of about 0.05 to 5% w/w based on the total weight of formulation, and
    wherein the treatment reduces the frequency or duration of spasm, or reduces the degree of pain.

3. The method of claim 1, wherein the cramp is a night cramp, and the treatment improves sleep quality.

4. The method of claim 2, wherein the spasm is a night spasm, and the treatment improves sleep quality.

5. The method claim 1, wherein the dipeptide composition comprises, based on the total weight of the dipeptide composition, about 10 to 40% w/w of one or more imidazole-containing dipeptides.

6. The method of claim 2, wherein the dipeptide composition comprises, based on the total weight of the dipeptide composition, about 10 to 40% w/w of one or more imidazole-containing dipeptides.

7. The method of claim 1, wherein the imidazole-containing dipeptide is carnosine or anserine.

8. The method of claim 2, where the imidazole-containing dipeptide is carnosine or anserine.

9. The method of claim 1, wherein the turmeric product contains, based on the total weight of the product, about 15 to 50% w/w of curcumin.

10. The method of claim 2, wherein the turmeric product contains, based on the total weight of the product about 15 to 50% w/w of curcumin.

11. The method of claim 9, wherein the turmeric product is a dried turmeric powder, a turmeric extract, a sub-micron turmeric, or a nano turmeric.

12. The method of claim 10, wherein the turmeric product is a dried turmeric powder, a turmeric extract, a sub-micron turmeric, or a nano turmeric.

13. The method of claim 11, wherein the turmeric product is a sub-micron turmeric or nano turmeric.

14. The method of claim 12, wherein the turmeric product is a sub-micron turmeric or nano turmeric.

15. The method of claim 12, wherein the ancient peat minerals contain trace mineral elements selected from aluminium, antimony, arsenic, barium, beryllium, bismuth, boron, bromine, cadmium, calcium, carbon, cerium, cesium, chloride, chromium, cobalt, copper, dysprosium, erbium, europium, fluoride, gadolinium, gallium, germanium, gold, hafnium, holmium, indium, iodine, iridium, iron, lanthanum, lead, lithium, lutetium, magnesium, manganese, mercury, molybdenum, neodymium, nickel, niobium, nitrogen, osmium, oxygen, palladium, phosphorous, platinum, potassium, praseodymium, rhenium, rhodium, rubidium, ruthenium, samarium, scandium, selenium, silicon, silver, sodium, strontium, sulfur, tantalum, tellurium, terbium, thallium, thorium, thulium, tin, titanium, tungsten, vanadium, ytterbium, yttrium, zinc, and zirconium.

16. The method of claim 2, wherein the ancient peat minerals contain trace mineral elements selected from aluminum, antimony, arsenic, barium, beryllium, bismuth, boron, bromine, cadmium, calcium, carbon, cerium, cesium, chloride, chromium cobalt, copper dysprosium, erbium europium, fluoride, gadolinium, gallium, germanium, gold, hafnium, holmium, indium, iodine, iridium, iron, lanthanum, lead, lithium, lutetium, magnesium, manganese, mercury, molybdenum, neodymium, nickel, niobium, nitrogen, osmium, oxygen, palladium, phosphorus, platinum, potassium, praseodymium, rhenium, rhodium, rubidium, ruthenium, samarium, scandium, selenium, silicon, silver, sodium, strontium, sulfur, tantalum, tellurium, terbium, thallium, thorium, thulium, tin, titanium, tungsten, vanadium, ytterbium, yttrium, zinc, and zirconium.

* * * * *